United States Patent
Peterson

(10) Patent No.: US 7,682,372 B2
(45) Date of Patent: Mar. 23, 2010

(54) SEQUENTIAL TISSUE FORCEPS FOR USE IN TISSUE FASTENING

(75) Inventor: James A. Peterson, Edina, MN (US)

(73) Assignee: Incisive Surgical, Inc., Plymouth, MN (US)

(*) Notice: Subject to any disclaimer, the term of this patent is extended or adjusted under 35 U.S.C. 154(b) by 788 days.

(21) Appl. No.: 11/316,322

(22) Filed: Dec. 22, 2005

(65) Prior Publication Data
US 2006/0135988 A1 Jun. 22, 2006

Related U.S. Application Data

(60) Provisional application No. 60/638,761, filed on Dec. 22, 2004.

(51) Int. Cl.
*A61B 17/50* (2006.01)
(52) U.S. Cl. .................................... 606/211
(58) Field of Classification Search ............. 606/144, 606/210, 211, 142, 143, 205–208, 213, 216, 606/219; 227/175.1, 176.1
See application file for complete search history.

(56) References Cited

U.S. PATENT DOCUMENTS

| | | | |
|---|---|---|---|
| 2,214,984 A | 9/1940 | Bachmann | |
| 3,653,389 A | 4/1972 | Shannon | |
| 4,950,281 A | 8/1990 | Kirsch et al. | |
| 5,520,704 A | 5/1996 | Castro et al. | |
| 5,565,004 A * | 10/1996 | Christoudias | 606/207 |
| 5,976,161 A * | 11/1999 | Kirsch et al. | 606/149 |
| 6,283,984 B1 | 9/2001 | Ray | |
| 6,685,725 B2 | 2/2004 | Attinger et al. | |
| 6,726,705 B2 | 4/2004 | Peterson et al. | |
| 6,863,679 B1 * | 3/2005 | Aaron | 606/210 |
| 7,238,195 B2 * | 7/2007 | Viola | 606/219 |
| 2002/0111641 A1 | 8/2002 | Peterson et al. | |
| 2003/0236551 A1 | 12/2003 | Peterson | |
| 2004/0059377 A1 | 3/2004 | Peterson et al. | |
| 2004/0059378 A1 | 3/2004 | Peterson et al. | |
| 2005/0085857 A1 | 4/2005 | Peterson et al. | |
| 2005/0182444 A1 | 8/2005 | Peterson et al. | |

\* cited by examiner

*Primary Examiner*—Todd E Manahan
*Assistant Examiner*—Lindsey Bachman
(74) *Attorney, Agent, or Firm*—Patterson, Thuente, Skaar & Christensen, P.A.

(57) ABSTRACT

A sequential surgical forceps is adapted to sequentially grasp tissue on opposed sides of a tissue interface and then present the tissue for capture and closure by a surgical fastening apparatus. The sequential tissue forceps comprises a first arm, a second arm and central arm wherein both the first arm and the second arm are sequentially closed with respect to the central arm. The first arm, second arm and central arm preferably comprise tips having a gripping structure to facilitate tissue capture and retention. The central arm includes structure that defines a mating interface to allow for selective positioning of the sequential tissue forceps and any captured tissue with respect to a surgical fastening apparatus. In this way, the tissue forceps is able to consistently manipulate and present wound tissue relative to the surgical fastening apparatus.

7 Claims, 15 Drawing Sheets

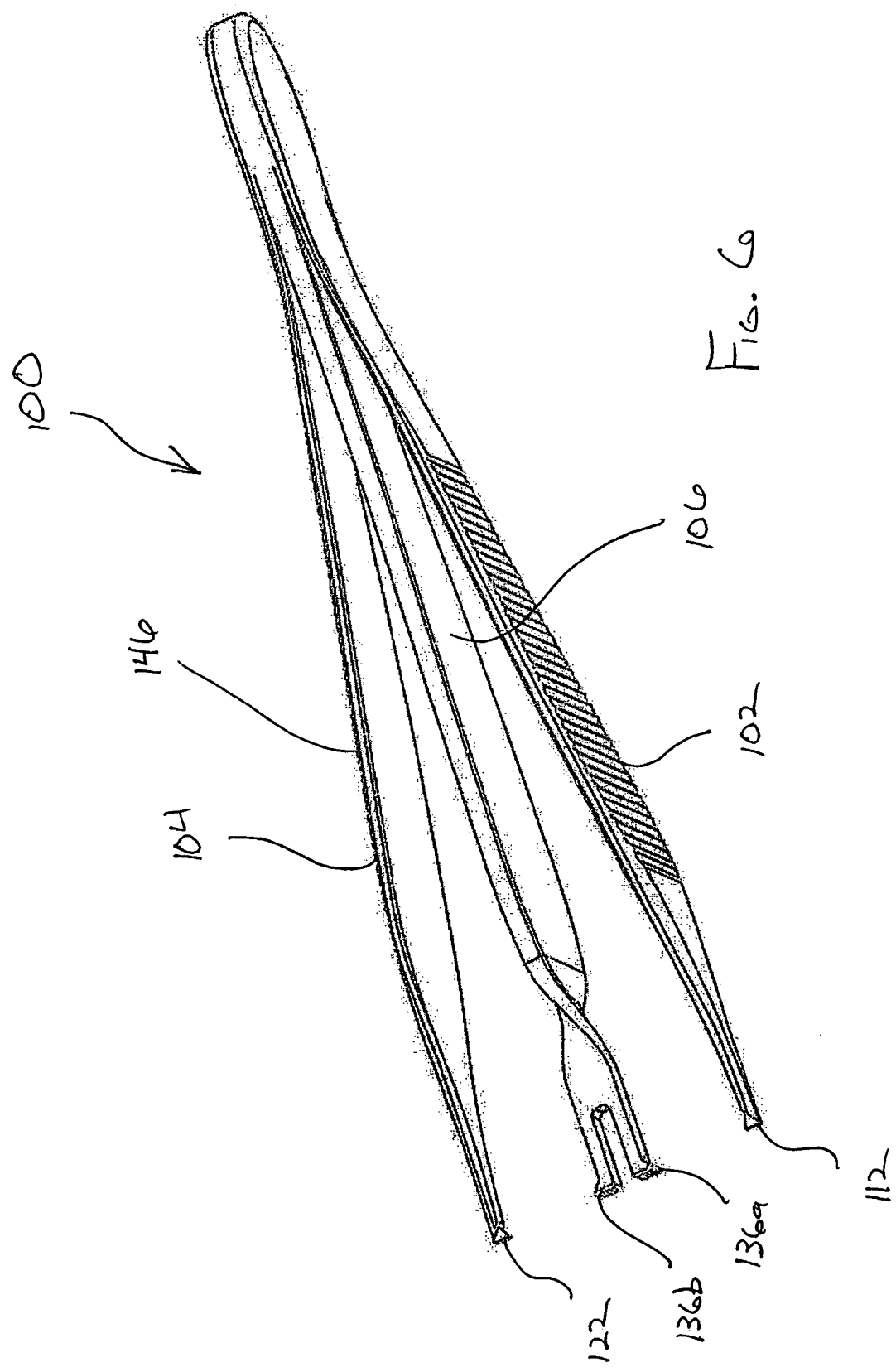

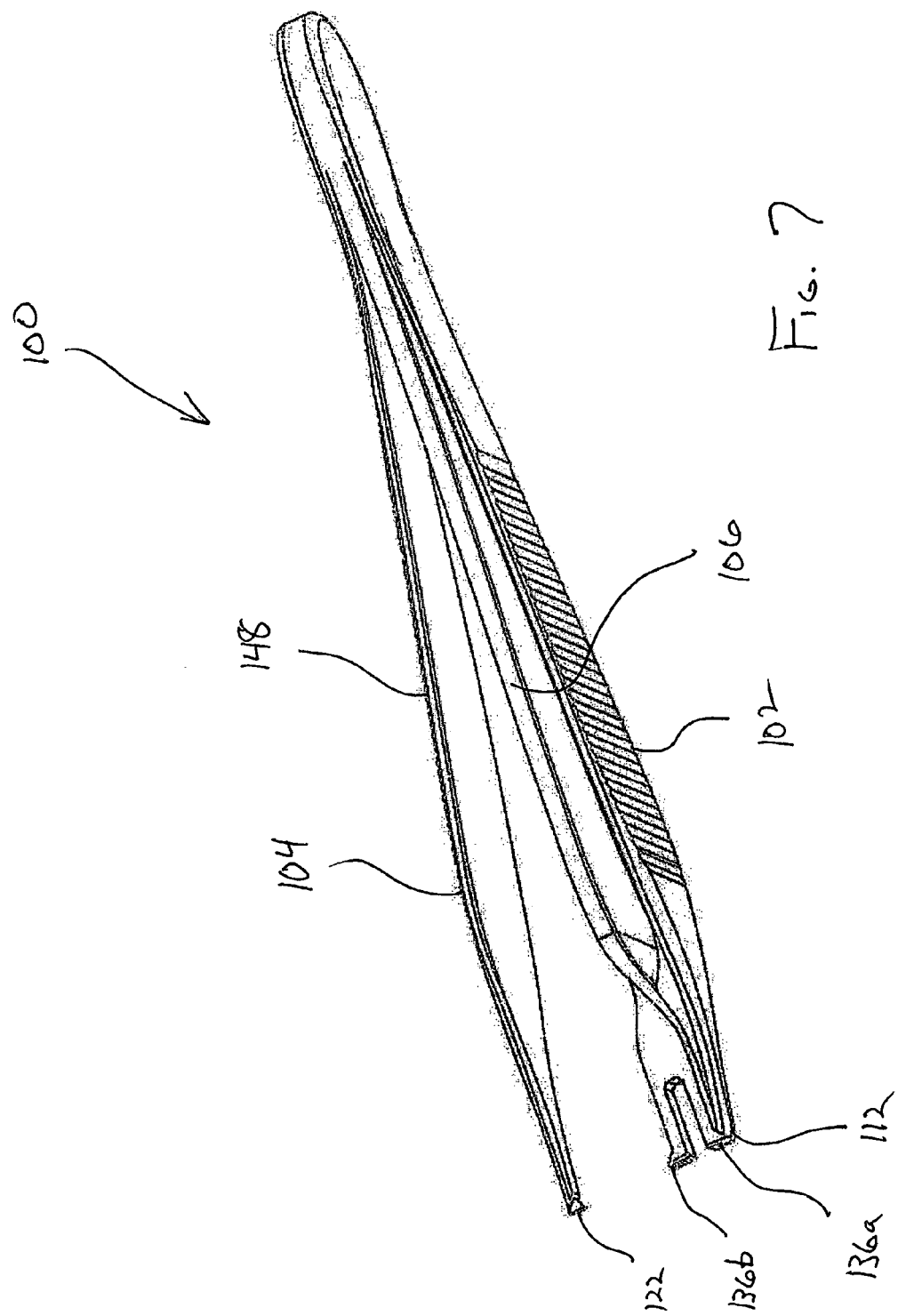

SEQUENTIAL TISSUE FORCEPS FOR USE IN TISSUE FASTENING

PRIORITY CLAIM

The present application claims priority to U.S. Provisional Application No. 60/638,761 filed Dec. 22, 2004, and entitled, "SEQUENTIAL TISSUE FORCEPS THAT INTERFACES WITH A SURGICAL FASTENING APPARATUS," which is incorporated by reference in its entirety.

FIELD OF THE INVENTION

The present invention relates generally to the field of surgical instruments such as tissue forceps. More particularly, the present invention relates to a sequential tissue forceps capable of sequentially grasping and approximating opposed sides of a wound with a single instrument that also includes structure that mates with corresponding structure on a surgical fastening apparatus.

BACKGROUND OF THE INVENTION

When an opening in tissue is created either through an intentional incision or an accidental wound or laceration, biological healing of the opening commences through the proximity of the opposed living tissue surfaces. If the opening is very large or if its location subjects the wound to continual movement, a physician will seek to forcibly hold the sides of the opening in close proximity so as to promote the healing process.

A variety of surgical methods and devices are currently employed in forcibly closing and approximating tissue openings throughout the healing process. Examples include the use of elastic skin closures, sutures, staples, adhesive dressings and skin glue. Regardless of their construction or method of use, these wound closure modalities all seek to positively retain living tissue on opposed sides of the opening in closed relation throughout the healing process.

In general, use of the aforementioned wound closure modalities necessitates that a medical professional manipulate and/or approximate opposed sides of the tissue wound prior to and/or during deployment of the wound closure modality. In many situations, the medical professional uses one or more surgical forceps to grasp and retain the tissue during application of the wound closure modality. A typical surgical forceps can comprise a pair of grasping arms that are operably joined at an apex such that arm tips located distally from the apex can be brought into proximity by squeezing the grasping arm together. This typically requires two medical professionals to successfully achieve wound closure; one for tissue approximation and one for fastener deployment. In other alternative configurations such as, for example, configurations disclosed in U.S. Pat. No. 2,214,984 to Bachmann, U.S. Pat. No. 4,950,281 to Kirsch et al., U.S. Pat. No. 5,520,704 to Castro et al., U.S. Pat. No. 5,565,004 to Christoudias and U.S. Pat. No. 6,283,984 to Ray, a surgical forceps can comprise two grasping arms and a central arm such that both sides of tissue wound can be grasped and retained with a single forceps.

One recent advance in the field of wound closure comprises a bilateral wound closure method in which a bioabsorbable fastener is positioned for deployment within target tissue zones, defined within the dermal layers on opposed sides of a wound interface. Once deployed, the bioabsorbable fastener is not externally visible and no follow-up visit is required to remove the fastener once the wound has healed. This bilateral wound closure approach is commercially available as the Insorb® Subcuticular Skin Stapler manufactured by Incisive® Surgical, Inc. of Plymouth, Minn., and is described in U.S. Pat. No. 6,726,705, as well as in a series of pending U.S. patent applications Ser. Nos. 10/448,838 and 10/607,497, all of which are herein incorporated by reference to the extent not inconsistent with the present disclosure.

Through the development of the aforementioned bilateral wound closure approach, it has been discovered that the targeted dermal tissue can have a multitude of variables that effects the ability to effectively approximate tissue for purposes of effecting a wound closure. These variables can comprise thickness, stretch, and strength and can vary based upon the wound's location on the body, the patient's body type as well as the patient's age. As such, it would be advantageous to further improve on the ability to effectively close wounds by having an apparatus and method of implementing said apparatus so as to consistently manipulate and present a wound to a closure instrument.

SUMMARY OF THE INVENTION

The present invention pertains to a sequential surgical forceps adapted to sequentially grasp tissue on opposed sides of a tissue interface. Once grasped in a sequential manner, the tissue can then be presented for capture and closure by a surgical fastening apparatus. The complete procedure of approximation and closure of a tissue wound can be accomplished by a single operator. The sequential tissue forceps comprises a first arm, a second arm and central arm wherein both the first arm and the second arm are sequentially closed with respect to the central arm. The first arm, second arm and central arm preferably comprise tips having an improved gripping surface to facilitate tissue capture and retention. In some embodiments, the central arm comprises a pair of tips wherein a gap is presented between the tips that defines a mating interface to allow for selective positioning of the sequential tissue forceps and any captured tissue with respect to a surgical fastening apparatus. In this way, the present invention is able to consistently manipulate and present wound tissue to the surgical fastening apparatus. In another embodiment, the sequential tissue forceps does not include a defined mating interface on the center arm but still provides for bilateral tissue capture and retention in a sequential manner using the sequential tissue forceps.

In one aspect, the present invention comprises a surgical tissue forceps apparatus having a first arm, a second arm and a central arm. The first arm, second arm and central arm are operably joined at an apex. The first arm and second arm are oriented on opposed sides of the central arm such that a first spring constant with respect to the first arm and the central arm is different from a second spring constant with respect to the second arm and the central arm. By varying the spring constant between the first and second spring constant, the surgical tissue forceps apparatus can be adapted so as to sequentially close the first arm and then the second arm with respect to the central arm. Through such a sequential closure of the first arm and second arm relative to the central arm, tissue on opposed sides of a wound can be sequentially grasped, retained and approximated under selective control of the user operating the present invention.

In one embodiment, the central arm comprises a defined mating interface at the tip portion of the central arm. The interface cavity is adapted to interface with corresponding structure preferably defined on a head portion of a surgical closure instrument so as to present the opposed sides of the tissue wound for closure with the surgical closure instrument.

In another aspect, the present invention comprises a method of sequentially approximating opposed sides of a tissue wound in preparation and anticipation of closing the wound with a surgical fastener. Using a sequential tissue forceps, a first side of a tissue wound is operably grasped and retained. Next, a second side of a tissue wound is operably grasped and retained with the same tissue forceps. Once both the first and second sides of tissue have been captured, the sequential tissue forceps is matingly interfaced with a surgical closure instrument, such that the tissue forceps selectively positions both the first and second sides of tissue with respect to the surgical fastening instrument.

In another aspect, the present invention comprises a wound closure system. The wound closure system comprises a sequential tissue forceps and a surgical closure instrument wherein the sequential tissue forceps is operably adapted so as to interface with the surgical closure instrument such that opposed sides of a tissue wound are grasped, retained and manipulated for consistent presentation of the wound tissue for closure by the surgical closure instrument.

The above summary of the various embodiments of the invention is not intended to describe each illustrated embodiment or every implementation of the invention. The figures in the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 6 is a perspective view of an embodiment of a sequential tissue forceps of the present invention in an open disposition.

FIG. 7 is a perspective view of the sequential tissue forceps of FIG. 6 in a partially-closed disposition.

Figure 1:
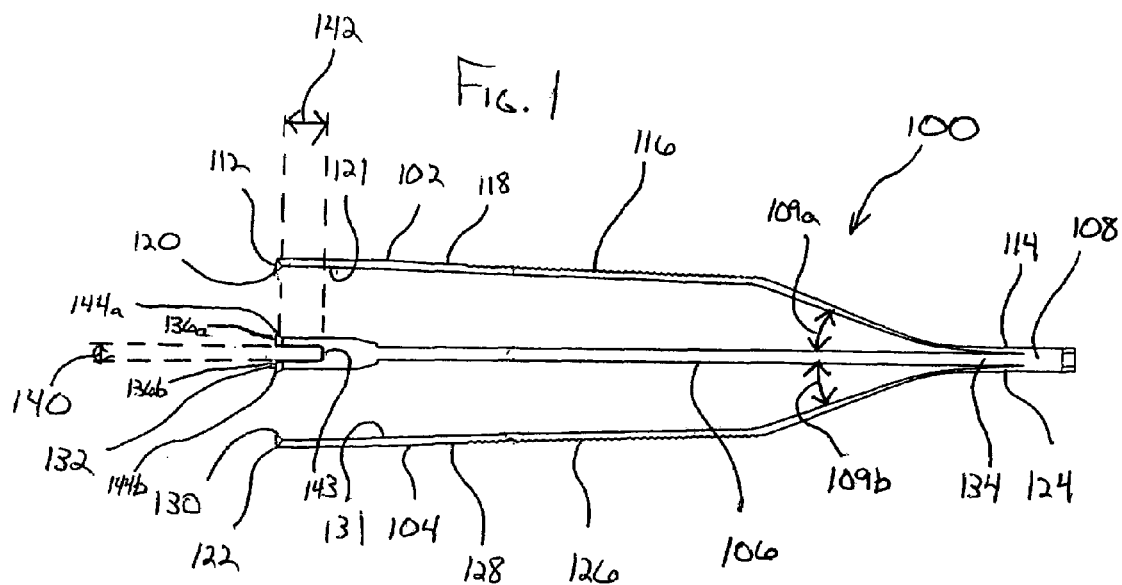
FIG. 1 is a plan view of an embodiment of a sequential tissue forceps of the present invention.
Figure 2:
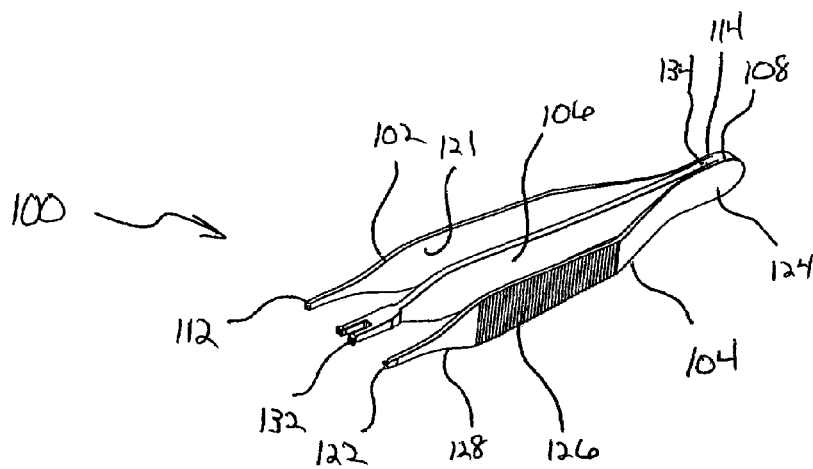
FIG. 2 is a perspective view of the sequential tissue forceps of FIG. 1.
Figure 3:
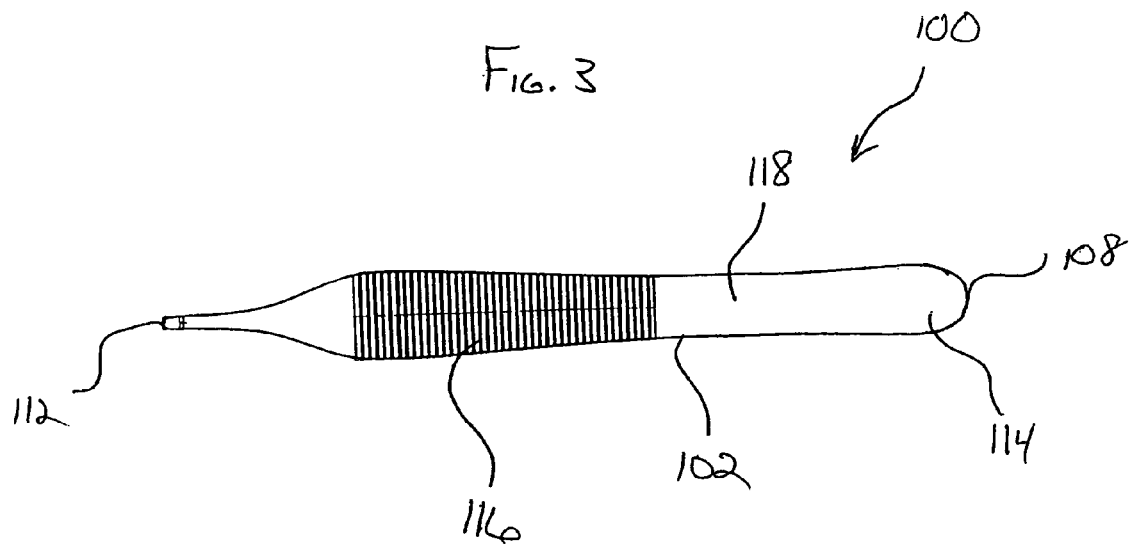
FIG. 3 is a side view of the sequential tissue forceps of FIG. 1.
Figure 4:
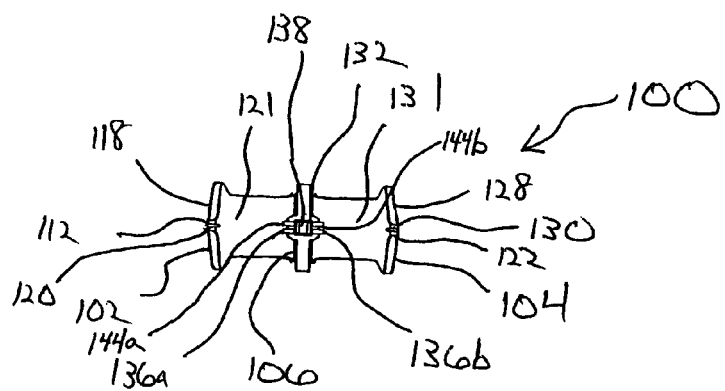
FIG. 4 is an end view of the sequential tissue forceps of FIG. 1 in an open configuration.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENTS

As illustrated in FIGS. 1, 2, 3 and 4, a sequential tissue forceps 100 of the present invention can comprise a first arm 102, a second arm 104 and a central arm 106. Sequential tissue forceps 100 can be fabricated of any material suitable for use in a surgical setting such as, for example, stainless steel, carbon fiber, medical grade polymers and combinations thereof. In one representative embodiment, sequential tissue forceps 100 can be fabricated of 400 series, high chromium stainless steel that has been annealed and tempered to provide desired performance characteristics as will be subsequently described. In some embodiments, sequential tissue forceps 100 is fabricated of a material capable of repeated sterilization with sterilization equipment such as, for example, an autoclave. Sequential tissue forceps 100 can be fabricated so as to comprise a unitary structure using a suitable molding or casting process. Alternatively, sequential tissue forceps 100 can be fabricated by operably joining two conventional forceps using a suitable joining process such as, for example, a welding process, wherein a first forceps comprises the first arm 102 and a first portion of the central arm 106 while a second forceps comprises the second arm 104 and a second portion of the central arm 106.

Regardless of fabrication method or material, first arm 102, second arm 104 and central arm 106 are operably connected at an apex 108. First arm 102 and central arm 106 define a first grasping angle 109*a* while second arm 104 and central arm 106 define a second grasping angle 109*b*. In one embodiment, sequential tissue forceps 100 is fabricated such that a first spring constant associated with first grasping angle 109*a* is less than a second spring constant associated with second grasping angle 109*b*. The first spring constant and second spring constant can be selectively chosen and varied during fabrication by varying the thickness of first arm 102 and second arm 104 or by varying the angles defined by first grasping angle 109*a* and second grasping angle 109*b* or by varying the material properties such as by selective hardening and tempering of metal. In one presently contemplated embodiment, the first spring constant and second spring constant are imparted to sequential tissue forceps 100 by casting the sequential tissue forceps from 400 series high-chromium stainless steel, stress relieving the forceps by application of heat up to about 2500° C., slowly cooling the forceps, tempering the forceps by application of heat to about 600° C. to restore hardness followed by an immediate quenching of the forceps in liquid nitrogen. In addition to providing for the first and second spring constants and material hardness, suitable fabrication techniques of the preferred embodiment impart a non-scissoring action on the first arm 102, second arm 104 and central arm 106 such that the movement of the various arms preferably resides substantially within a common plane, thereby maintaining lateral stability during normal use and avoiding any significant overlap and/or misalignment of the arm tips when the arm tips are approximated.

Figure 5A:
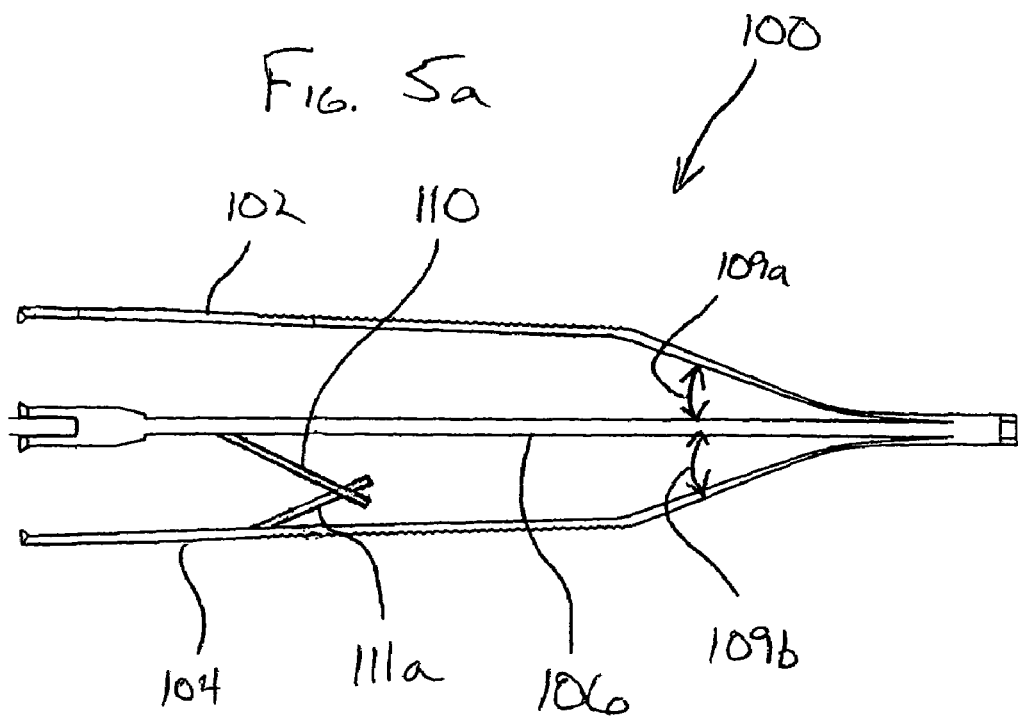
FIG. 5*a* is a plan view of an alternative embodiment of a sequential tissue forceps of the present invention.
Figure 5B:
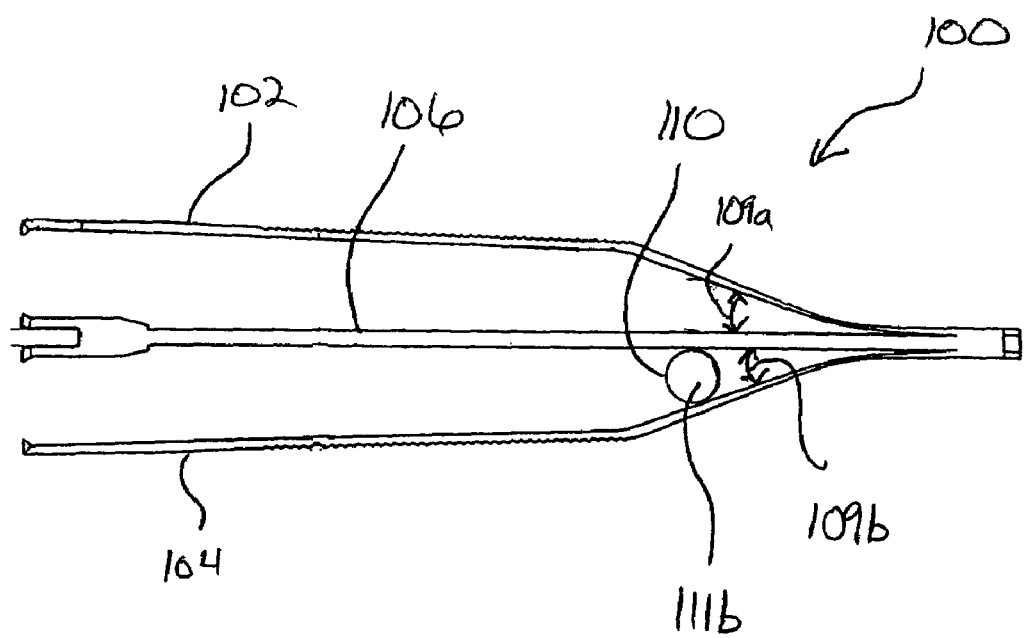
FIG. 5*b* is a plan view of an alternative embodiment of a sequential tissue forceps of the present invention.

Alternatively, or in addition to varying the first and second spring constants through selective fabrication, a compressible member 110 can be fixedly mounted, for example, between second arm 104 and central arm 106 such that it spans at least a portion of the second grasping angle 109b as illustrated in FIGS. 5a and 5b. Compressible member 110 can comprise any of a variety of alternative configurations such as, for example, a leaf spring 111a as seen in FIG. 5a or a compressible polymer 111b as seen in FIG. 5b. Compressible member 100 can further comprise other suitable configurations such as, for example, a compression spring, a torsion spring and the like. In some representative embodiments, compressible member 110 can comprise materials of construction capable of surviving a sterilization and/or autoclaving procedure such as, for example, stainless steel. While a single compressible member 110 is described and depicted in FIGS. 5a and 5b, it will also be recognized that a pair of compressible members 110 possessing differing compression properties can be utilized, to achieve different effective spring constants associated with the grasping angles 109a and 109b. It will also be recognized that a plurality of compressible members 110 may be used within each of the grasping angles 109a, 109b, either longitudinally along the arms 102, 104 or 106 or stacked there between.

First arm 102 is generally defined by a first tip 112 and a first interconnecting end 114. First arm 102 can preferably include a first grip enhancement 116 on a first manipulation surface 118. First grip enhancement 116 can comprise a variety of suitable surface treatments for promoting an operator's grip such as, for example, machined or molded ridges, grooves and other friction enhancers or the application of a grippable rubber or rubber-like polymer. First tip 112 similarly can include a first gripping member 120 on a first interior surface 121 selected to enhance the gripping capability of the first arm 102 with respect to tissue capture. First gripping member 120 can comprise any of a variety of gripping shapes and structures including a projecting member, a piercing member and/or surface treatments such as, for example, machined or molded ridges, grooves and other friction enhancers or the application of a grippable rubber or rubber-like polymer.

In another embodiment, second arm 104 is constructed to resemble first arm 102 such that the second arm 104 is defined by a second tip 122 and a second interconnecting end 124. Second arm 104 preferably can include a second grip enhancement 126 on a second manipulation surface 128. Second grip enhancement 126 can substantially resemble first grip enhancement 116 and may comprise suitable surface treatments such as, for example, machined or molded ridges, grooves and other friction enhancers or the application of a grippable rubber or rubber-like polymer, as previously described with respect to first grip enhancement 116. Second tip 122 can include a second gripping member 130 on a second interior surface 131 substantially resembling first gripping member 120 wherein said second tip 122 is selected to enhance the gripping capability of the second arm 104 with respect to tissue capture. Second gripping member 130 can comprise any of a variety of gripping shapes and structures including a projecting member, a piercing member and/or surface treatments such as, for example, machined or molded ridges, grooves and other friction enhancers or the application of a grippable rubber or rubber-like polymer.

Central arm 106 is generally defined by a tip portion 132 and a central interconnecting end 134. In one representative embodiment, tip portion 132 comprises a pair of dual tips 136a, 136b separated by a mating interface 138. Mating interface 138 is generally defined by an interface width 140, an interface depth 142 and an interface wall 143. Dual tips 136a, 136b preferably each comprise a central tip gripping surface 144a, 144b similar to gripping surface 120 and second gripping surface 130.

In operation, a medical professional preferably grasps and operates the sequential tissue forceps 100 with a single hand. During use and operation of sequential tissue forceps 100, the medical professional generally squeezes and manipulates sequential tissue forceps 100 between an open disposition 146 as illustrated in FIG. 6, a partially-closed disposition 148 as illustrated in FIG. 7 and a fully-closed disposition 150 as illustrated in FIG. 8.

With respect to the open disposition 146 shown generally in FIG. 7, the sequential tissue forceps 100 assumes and remains in open disposition 146 at all times in which a squeezing bias is not introduced on the first arm 102 and second arm 104 including times prior to and following use such as, for example, shipment, storage, sterilization and disposal. Generally, open disposition 146 is maintained through the selection of first and second spring constants having a minimum value so as to define minimum compression forces required to direct either the first arm 102 or second arm 104 into proximity with central arm 106. In one presently preferred embodiment, a minimum compression force for directing either first arm 102 or second arm 104 into proximity with central arm 106 exceeds at least about 0.5 pounds and more preferably, exceeds about 0.6 pounds. By having a minimum compression force exceeding at least about 0.5 pounds, closure of either first arm 102 or second arm 104 into proximity with central arm 106 must be accomplished through a squeezing action by a user as opposed to collapsing or closing by itself.

With respect to FIG. 7 depicting the partially-closed disposition 148, first arm 102 is described as approaching central arm 106 in the following discussion though it will be understood that the discussion is relevant to second arm 104 as well as either first arm 102 or second arm 104 can approach central arm 106 depending upon which of the first and second spring constants is less. Squeezing first arm 102 and second arm 104 with a compression force exceeding the minimum compression force defined by the first spring constant, and assuming that the first spring constant is less than the second spring constant, results in first tip 112 approaching dual tip 136a such that first tip 112 and dual tip 136a are either in contact or in close physical proximity. During this initial squeezing of first arm 102 and second arm 104, second arm 104 remains generally stationary and set apart from central arm 106 as the initial compression force exceeds only the first spring constant. The initial compression force to achieve partially-closed disposition 148 preferably, exceeds about 0.5 pounds as previously discussed and preferably does not exceed about 1.0 pounds.

Figure 8:
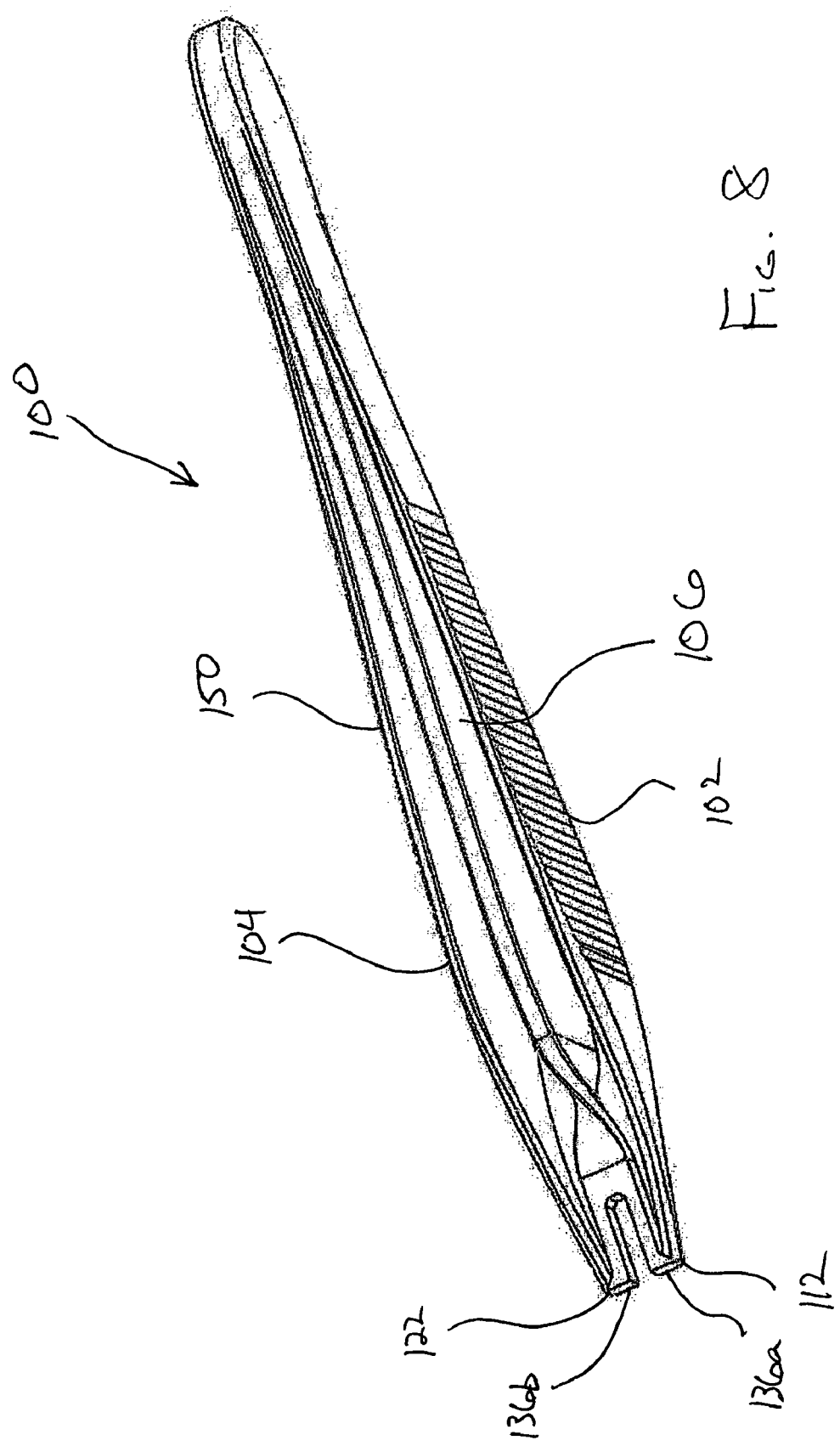
FIG. 8 is a perspective view of the sequential tissue forceps of FIG. 6 in a fully-closed disposition.

Once first arm 102 has been fully squeezed such that first tip 112 is in abutting contact and/or proximity with the dual tip 136a, further squeezing on the first arm 102 and second arm 104 in excess of the second compression force defined by the second spring constant effectively causes second tip 122 to approach dual tip 136b so as to assume fully-closed disposition 150 as illustrated in FIG. 8. The second spring constant preferably defines the second compression force so as to be accomplished with a squeezing force that can be easily accomplished by a medical professional. For example, a suitable second compression force can range from about 1.0 pounds to about 2.0 pounds, and more preferably ranges from about 1.5 pounds to about 1.85 pounds. In the embodiment in which second arm 104 includes compression member 110, the further squeezing causes compression of the compressible member 110 as part of this process. Through such continued, further squeezing, second tip 122 approaches and ultimately contacts the dual tip 136b. When fully squeezed, first tip 112 and second tip 122 preferably are maintained and spaced apart by at least the interface width 140 plus any additional thickness from captured tissue.

When selecting the first compression force and second compression forces, several factors must be considered. First, the required compression forces should be high enough that neither the first arm 102 nor second arm 104 close by themselves when not in use to grasp tissue. In addition, the required compression forces should be high enough that tissue can be retained between either the first arm 102 and central arm 106 or between the second arm 104 and central arm 106 such that the sequential forceps 100 can be repositioned to grasp tissue apart from and/or opposed to the tissue which is already grabbed. However, the required compression forces should not be so high as to require compression forces that would lead to tissue damage with captured tissue or to cause operator fatigue during use. Preferably, the compression forces selected for the second compression force and the first compression force are selectively chosen such that a ratio of the second compression force to the first compression force ranges from about 1.5:1 to about 3.5:1, and more preferably from about 2:1 to about 3:1.

In one embodiment, the sequential tissue forceps 100 can provide for unique advantages relative to wound closure methods such as, for example, bilateral wound closure methods performed utilizing the Insorb® Subcuticular Skin Stapler available from Incisive® Surgical, Inc., of Plymouth, Minn., and as described in U.S. Pat. No. 6,726,705 and U.S. Patent Publications Nos. 2002/0111641A1, 2003/0236551A1, 2004/0059377A1 and 2005/0085857A1, all of which are herein incorporated by reference in their entirety.

Figure 9:
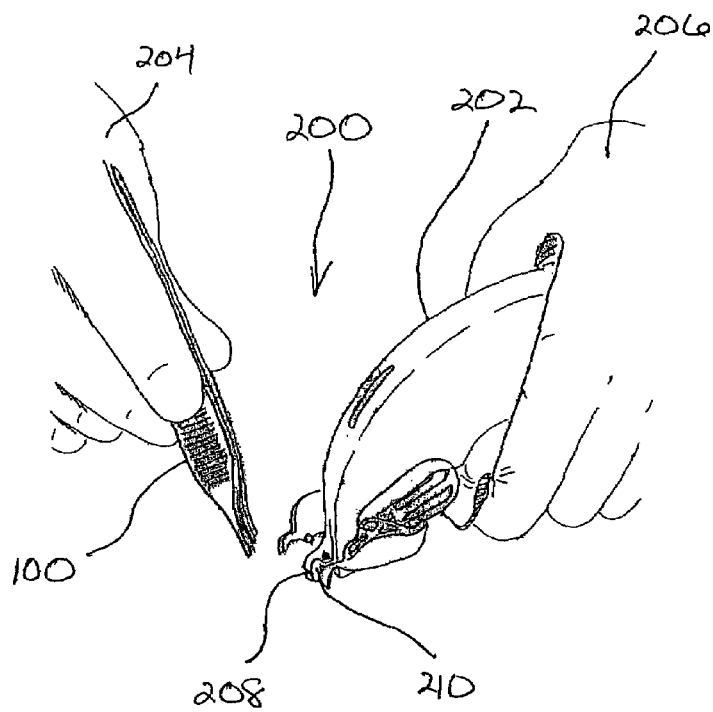
FIG. 9 is a perspective view of an embodiment of a skin fastening system for use by a medical professional.
Figure 10:
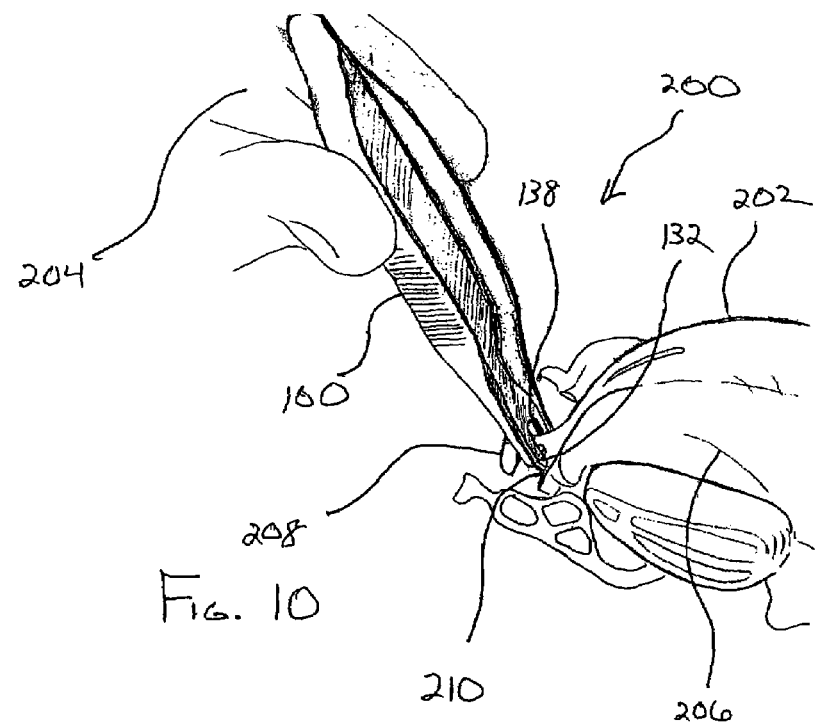
FIG. 10 is a perspective view of the skin fastening system of FIG. 9 for use by a medical professional.

A representative skin fastening system 200 as illustrated in FIGS. 9 and 10 can comprise sequential tissue forceps 100 and a skin stapler 202. In one preferred embodiment, skin stapler 202 can comprise the afore referenced Insorb® Subcuticular Skin Stapler. As illustrated in FIG. 9, operation of skin fastening system 200 can be accomplished with a single medical professional with the medical professional manipulating the sequential tissue forceps 100 with a first hand 204 and the skin stapler 202 with a second hand 206. With reference to FIGS. 9 and 10, skin stapler 202 can comprise an insertion head 208 having a nested capture region 210 adapted to receive the mating interface 138 for positioning the tip portion 132 relative to the insertion head 208.

As shown in FIGS. 11, 12, 13 and 14, skin fastening system 200 can be utilized to close a skin tissue wound 300. Initially, sequential tissue forceps 100 is positioned proximate to the tissue wound 300. Tissue wound 300 is generally defined by a tissue opening 302, a first tissue side 304 and a second tissue side 306. As described and illustrated, skin tissue wound 300 is externally located with reference to the human body, i.e., the skin. However, it will be understood by one of skill in the art that use and operation of the skin fastening system 200 and sequential tissue forceps 100 is not limited to skin wounds, closed either with external or subcuticular closure modalities, but can be similarly utilized to close internal wounds or to position or maintain tissue and/or organ positions internal to the human body.

Figure 11:
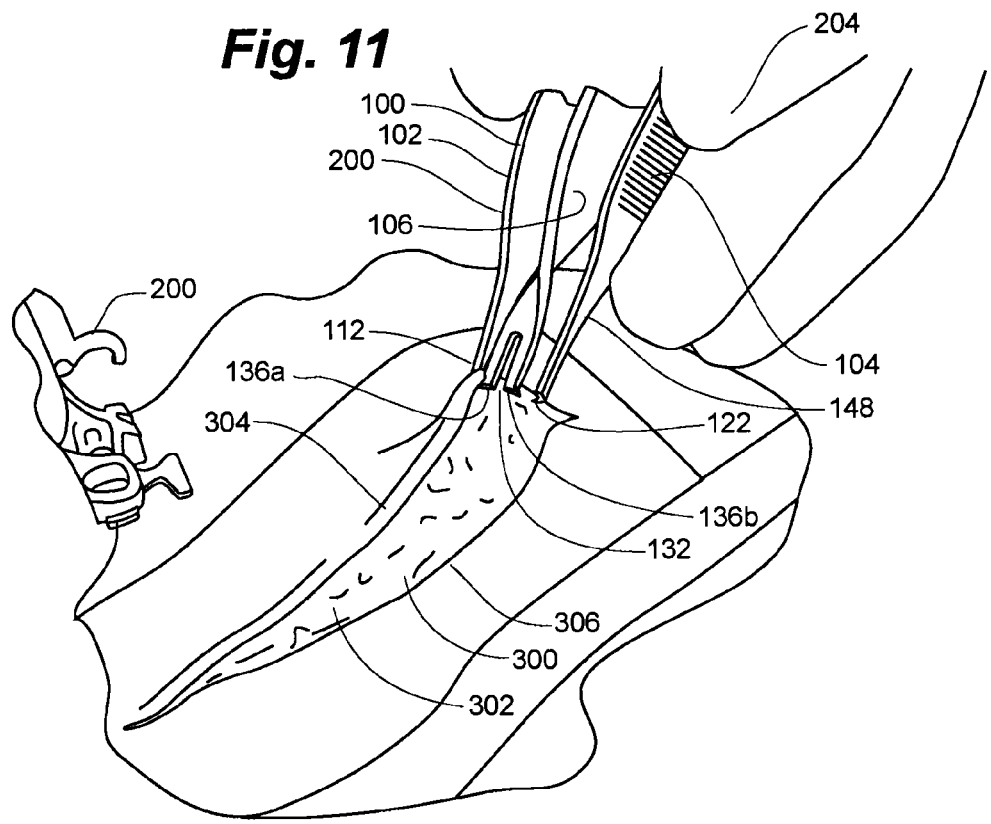
FIG. 11 is a perspective view of the sequential tissue forceps of FIG. 6 grasping tissue on a first side of a wound.

In a first operational step as shown in FIG. 11, sequential tissue forceps 100 is positioned in proximity to the first tissue side 304 such that tip portion 132 is located in the tissue opening 302 with the first tip 112 positioned external to the wound 300, and more specifically, external to first tissue side 304. An initial squeezing force exceeding at least about 0.5 pounds is applied to the first arm 102 and second arm 104 by first hand 204 such that the first tip 112 approaches or closes with respect to the dual tip 136a. As described previously, second tip 122 does not at this time approach the dual tip 136b due to the increased spring constant of the second spring constant between the second arm 104 and the central arm 106 such that sequential tissue forceps 100 assumes partially-closed disposition 148. As first tip 112 approaches dual tip 136a, first tissue side 304 is captured and retained between first tip 112 and dual tip 136a. First tip 112, first gripping member 120, dual tip 136a and central tip gripping surface 144a cooperatively retain first tissue side 304 as long as the compression force applied to first arm 102 and second arm 104 exceeds about 0.5 pounds.

Figure 12:
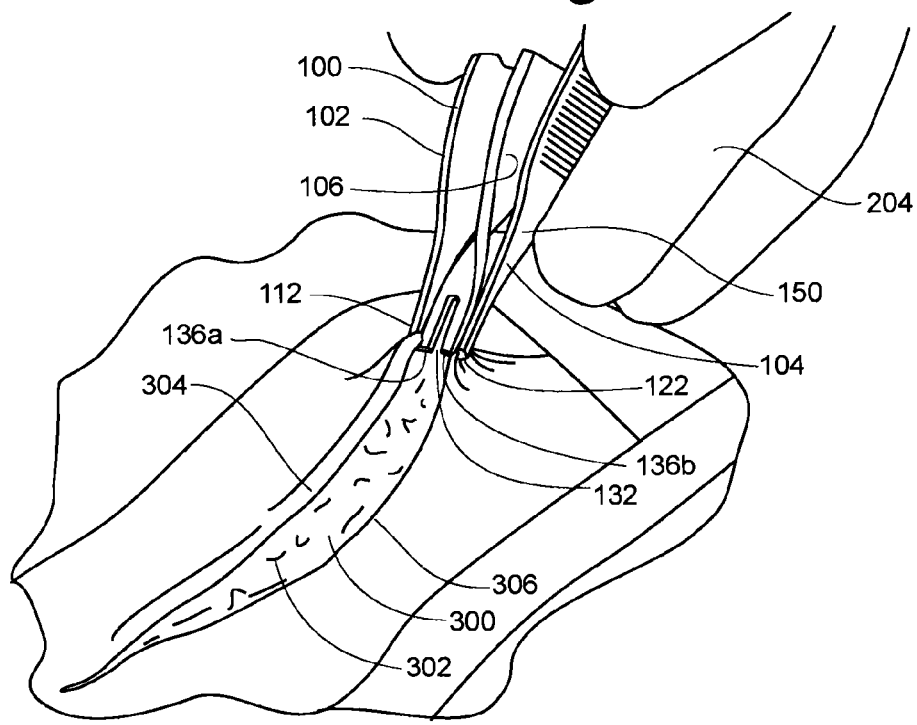
FIG. 12 is a perspective view of the sequential tissue forceps of FIG. 6 grasping tissue on a second side of the wound while retainably holding the first side of the wound.

Following the capture of first tissue side 304, tip portion 132 is positioned proximate the second tissue side 306 such that the second tip 122 is positioned external to second tissue side 306 as shown, while first tissue size 304 remains captured between first tip 112 and dual tip 136a. As the tip portion 132 is repositioned with respect to the second tissue side 306, the initial compression force used to capture the first tissue side 304 is maintained. Once the sequential tissue forceps 100 is properly positioned with respect to the second tissue side 306, the compression force applied to first arm 102 and second arm 104 is increased to an amount sufficient to overcome the second spring constant, generally between about 1.0 to about 2.0 pounds, between the second arm 104 and central arm 106. The increased compression force directs second tip 122 toward dual tip 136b. As second tip 122 approaches dual tip 136b, second tissue 306 is captured and retained as the sequential tissue forceps 100 assumes fully-closed disposition 150 as illustrated in FIG. 12. Second tip 122, second gripping member 130, dual tip 136b and central tip gripping surface 144b cooperatively retain second tissue side 306 as long as the compression force applied to first arm 102 and second arm 104 exceeds about 1.0 pounds. When second tip 122 has been closed with respect to the dual tip 136b, first tissue side 304 and second tissue side 306 are retainably captured on opposed sides of the tip portion 132 at a distance only slightly exceeding interface width 140.

Upon retainable capture of the first tissue side 304 and second tissue side 306 by the sequential tissue forceps 100, a medical professional is able to maintain the grip and positioning of first tissue side 304 and second tissue side 306 with a single hand, for example, first hand 204. At this point, the medical professional may utilize second hand 206 to retainably join first side 304 and second side 306 with a surgical fastener such as, for example, a fastener, a staple, a suture, steri-strips, an adhesive bandage and skin glue, used either individually or in combination, to retainably close tissue opening 302 so as to promote healing of wound 300. Alternatively, a second medical professional may assist in the surgical closure process.

Figure 13:
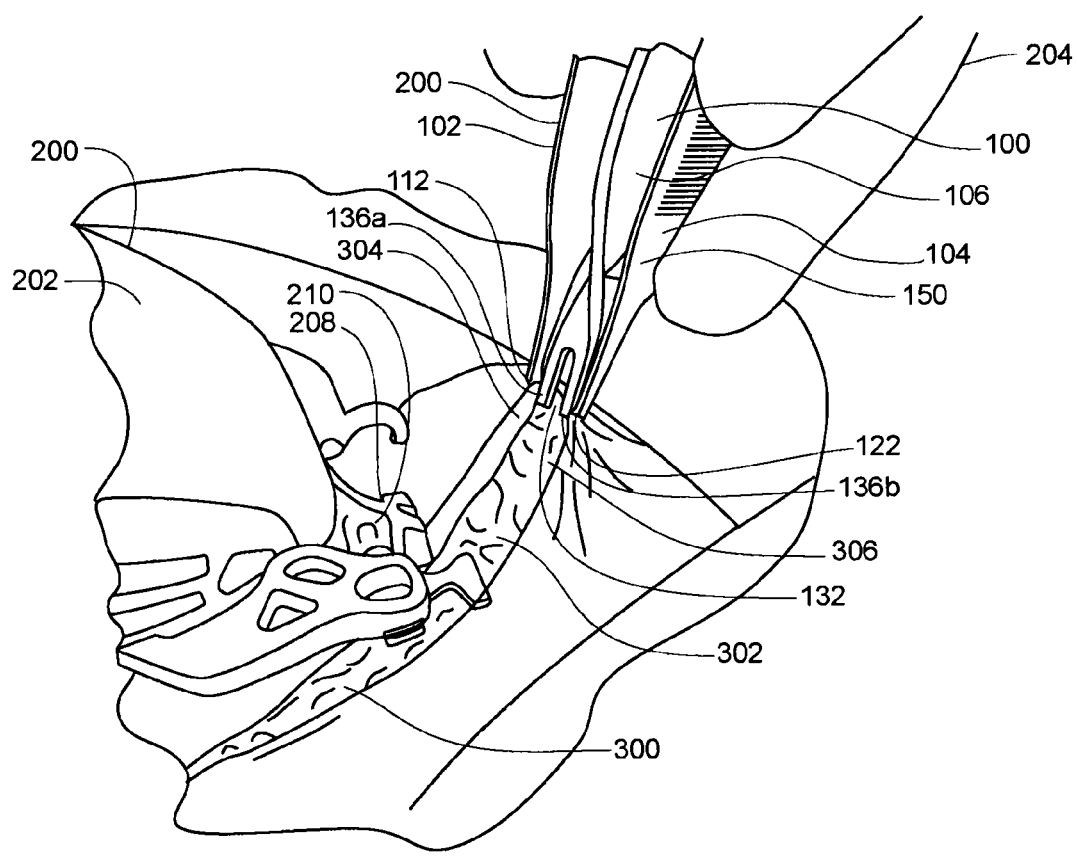
FIG. 13 is a perspective view of the sequential tissue forceps of FIG. 6 retainably holding the first and second sides of the wound while a surgical fastening instrument is positioned with respect to the wound by a medical professional.
Figure 14:
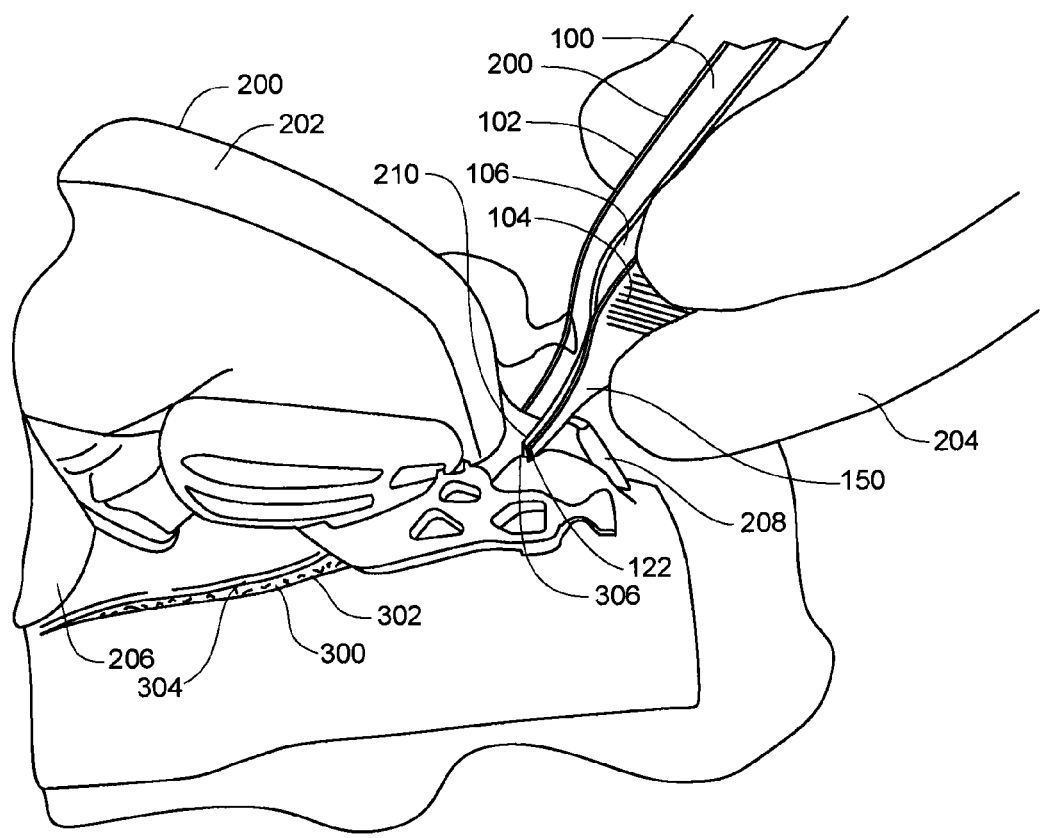
FIG. 14 is a perspective view of the sequential tissue forceps of FIG. 6 interfacing with an insertion head of the surgical fastening instrument such that the wound can be retainably closed with a medical fastener.

As illustrated in FIGS. 13 and 14, the medical professional can utilize the skin stapler 202, depicted as the Insorb® Subcuticular Skin Stapler, to close the wound 300. The insertion head 208 is positioned generally within the tissue opening 302. Insertion head 208 is positioned so as to reside generally below the captured first tissue side 304 and second tissue side 306. In this embodiment, the medical professional orients and positions the sequential tissue forceps 100, while still retaining first tissue side 304 and second tissue side 306, such that the mating interface 138 is slidably positioned into the nested capture region 210. When the mating interface 138 is positioned over the nested capture region 210, the mating interface 138 preferably is in abutting relation to the nested capture region 210 along the length of interface depth 142 such that the interface wall 143 is in physical contact with the insertion head 208. Through the interaction of nested capture region 210 and mating interface 138 including precise dimensioning of interface width 140 and interface depth 142, a point of tissue presentation is adjustably variable with respect to where the first tip 112, second tip 122 and dual tips 136a, 136b, are located with respect to the insertion head 208 when the sequential tissue forceps 100 and skin stapler 202 are fully nested as shown in FIG. 14.

Varying the point of tissue presentation with respect to the skin stapler 202 is especially advantageous due to differences in tissue thickness and stretch which can vary depending upon placement on the body such as, for example, the head region versus the stomach region, or based upon the body type of the patient such as, for example, male versus female, obese versus underweight, and the like.

Once first tissue side 304 and second tissue side 306 have been retainably positioned with respect to the insertion head 208, a fastener such as, for example, a dynamic bioabsorbable fastener as taught by U.S. Patent Publications Nos. 2004/0059378A1 and 2005/0182444A1, both of which are herein incorporated by reference in their entirety, is deployed by the skin stapler 202 to capture first side 304 and second side 306 so as to at least partially close wound 300. In addition or as an alternative, a complimentary fastener device such as, for example, a suture, an adhesive skin closure such as Steri-Strip™ brand closures available from Minnesota Mining and Manufacturing of Maplewood, Minn., an adhesive bandage such as Band-Aid® brand adhesive bandages available from Johnson & Johnson of New Brunswick, N.J., and skin glue such as Dermabond® brand liquid stitches available from Ethicon, Inc, a Johnson & Johnson company, can be applied to cooperatively maintain the closure of wound 300.

In another aspect of the present invention, skin stapler 202 and more specifically, insertion head 208 can be further adapted to promote the ability to selectively vary the point of tissue presentation between the sequential tissue forceps 100 and skin stapler 202. In one representative example shown in FIG. 15, insertion head 208 can be configured so as to provide a multiplicity of staged receiving portions 212a, 212b, 212c, each capable of individually, slidably interfacing with mating interface 138 and interface wall 143. Using sequential tissue forceps 100, a medical professional can capture first tissue side 304 and second tissue side 306 as previously described. The medical professional can then position the skin stapler 202 such that the insertion head 208 resides within the tissue opening 302 as previously described. Based upon factors such as, for example, professional experience and tissue variables such as thickness and conditions, the medical professional can determine the desired depth of tissue presentation with respect to where the first tip 112, second tip 122 and dual tips 136a, 136b position the first tissue side 304 and second tissue side 306 with respect to the insertion head 208. For example, abuttably positioning receiving portion 212a against interface wall 143 results in first tissue side 304 and second tissue side 306 being positioned at a deepest position relative to the insertion head 208. Similarly, abuttably positioning receiving portion 212b against interface wall 143 results in first tissue side 304 and second tissue side 306 being positioned at an intermediate depth relative to the insertion head 208 while abuttably positioning receiving portion 212c against interface wall 143 results in first tissue side 304 and second tissue side 306 being positioned at a shallowest position within the insertion head 208. The medical professional can selectively choose the depth of tissue presentation within the insertion head 208 based upon personal experience and preference as well as a variety of application or tissue related factors such as, for example, placement on the body such as, for example, the head region versus the stomach region, skin versus organ, wound retention versus tissue positioning or based upon the body type of the patient such as, for example, young versus old, male versus female, obese versus underweight, and the like.

Figure 15:
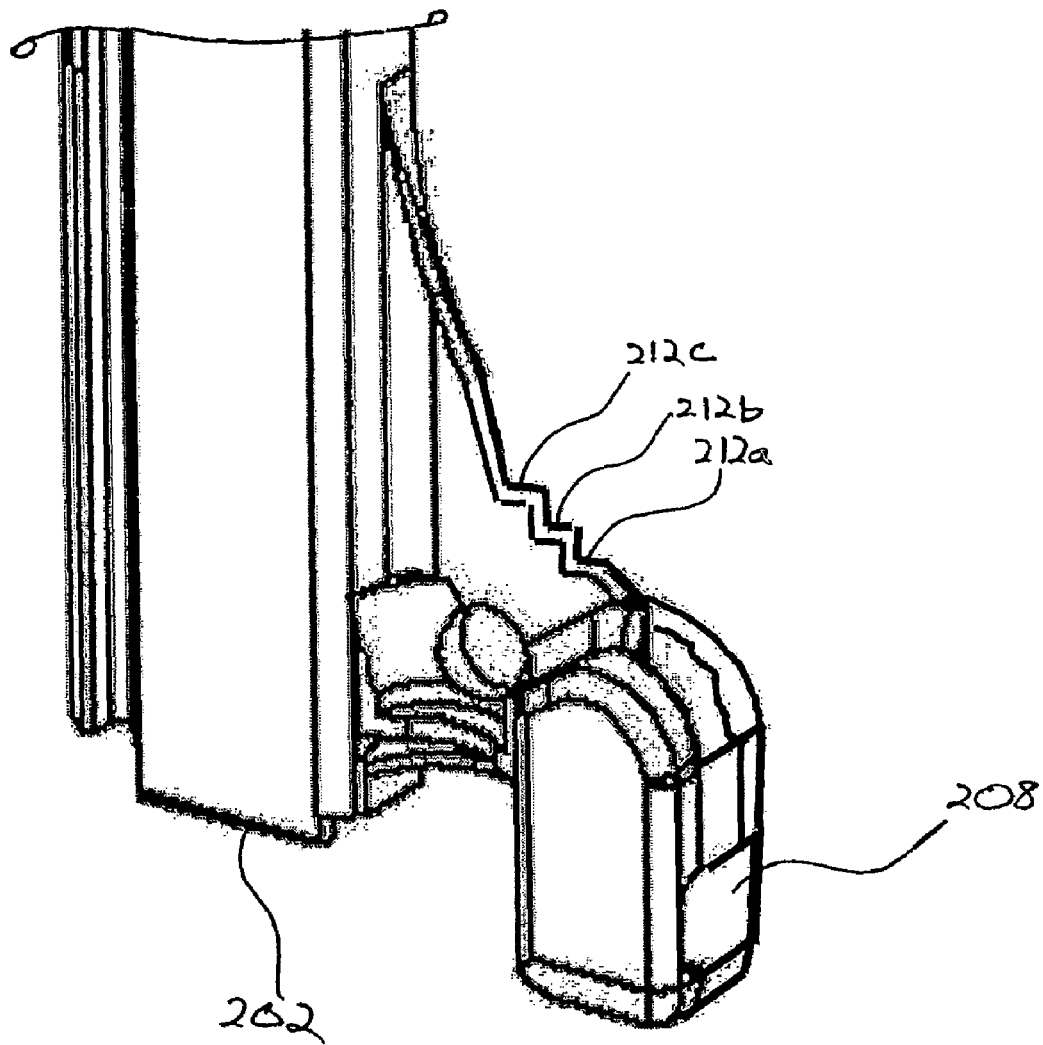
FIG. 15 is a perspective view of an embodiment of an insertion head for a surgical fastening instrument of the present invention.
Figure 16A:
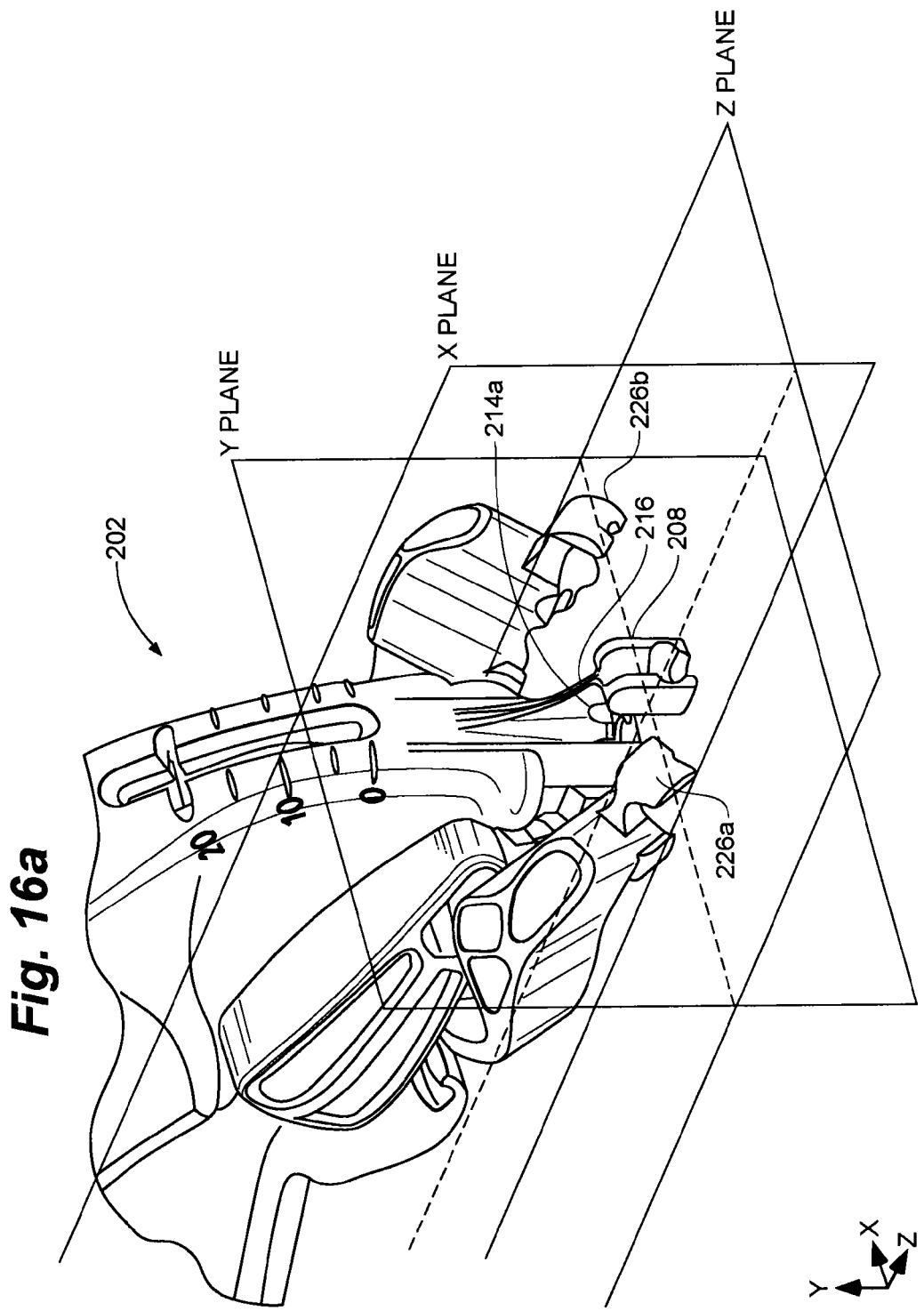
FIG. 16*a* is a perspective view of a surgical fastening instrument for use with a sequential tissue forceps of the present invention.
Figure 16B:
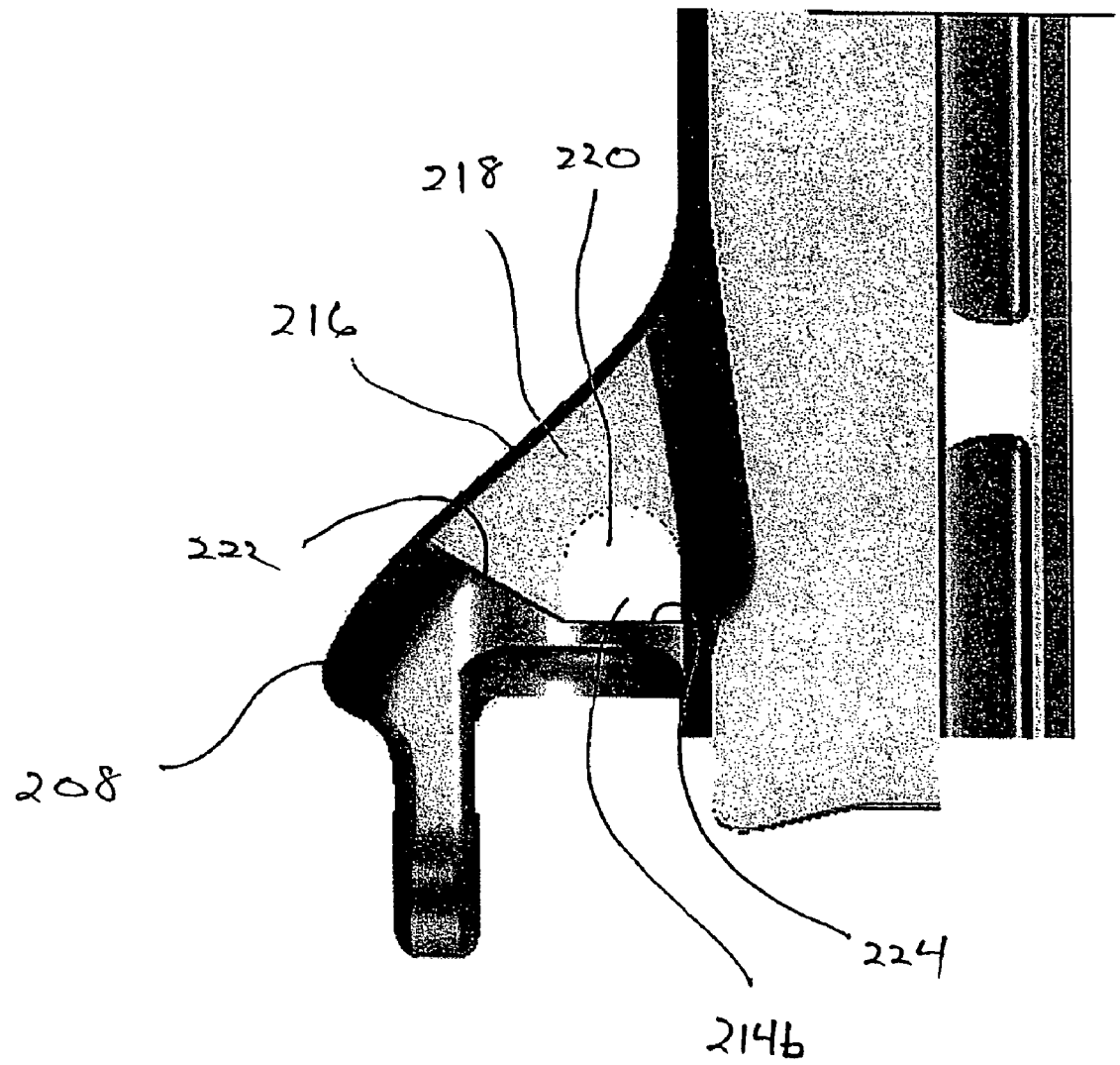
FIG. 16*b* is a side view of an insertion head of the surgical fastening instrument of FIG. 16*a*.
Figure 17:
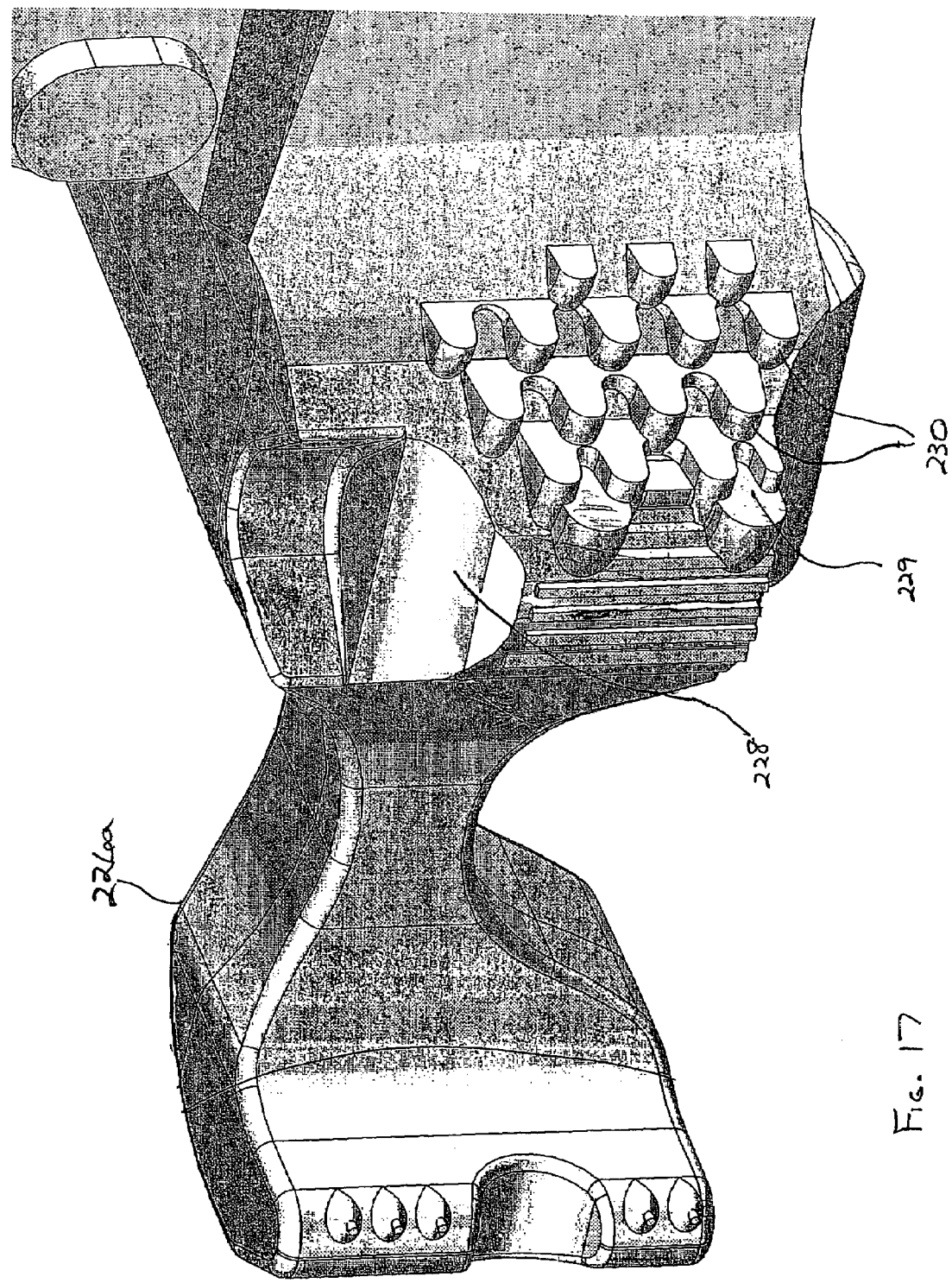
FIG. 17 is a perspective view of an capture arm on the surgical fastening instrument of FIG. 16*a*.
Figure 18:
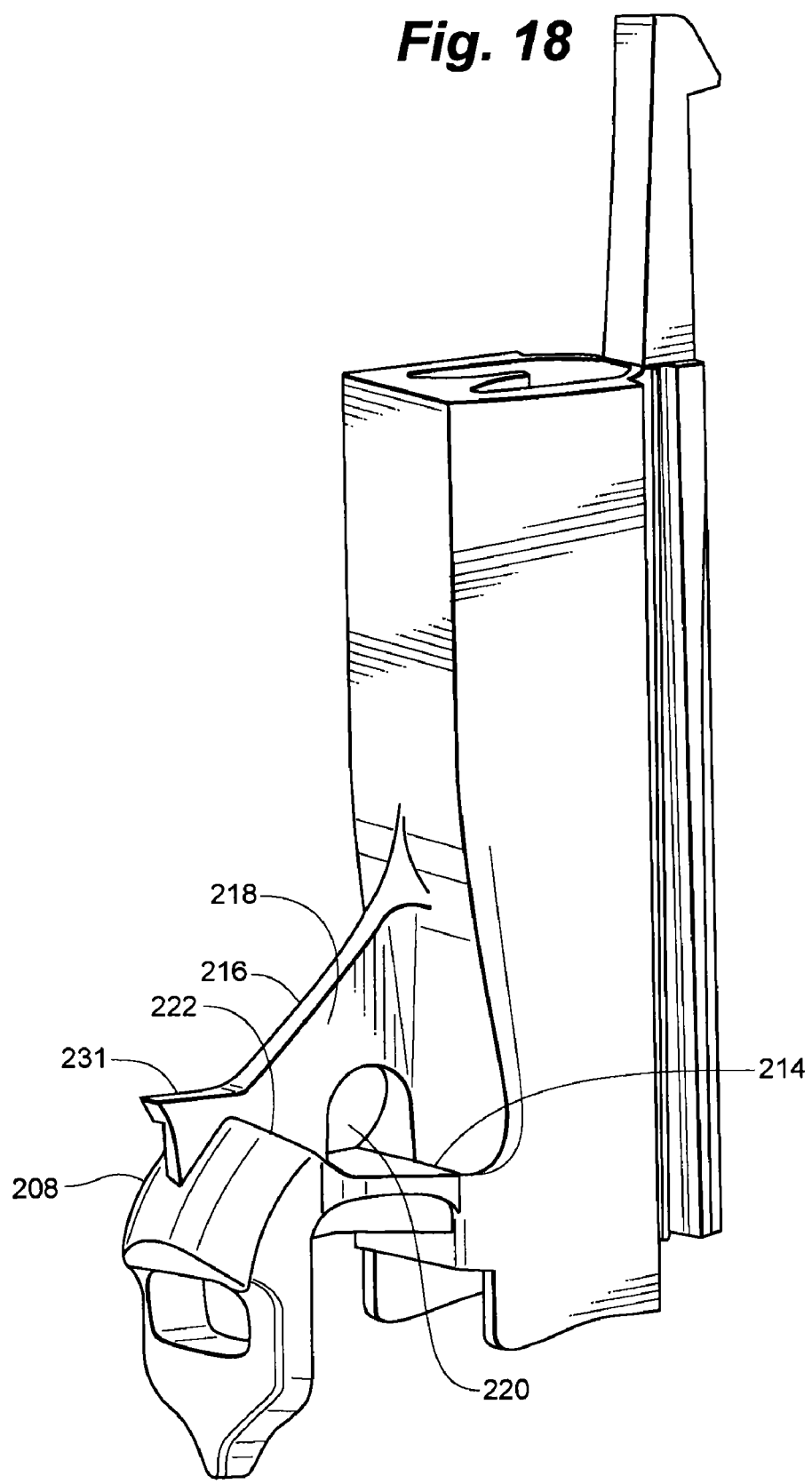
FIG. 18 is a perspective view of an embodiment of an insertion head for a surgical fastening instrument of the present invention.

In another aspect of the invention, use of the skin fastening system 200 can be promoted through configuration of the skin stapler 202 for consistent placement and presentation of the first tip 112, second tip 122 and dual tips 136a, 136b relative to the insertion head 208. As illustrated in FIGS. 16a and 16b, insertion head 208 can comprise a pair of positioning guides 214a, 214b on either side of a divider wall 216. The positioning guides 214a, 214b can each comprise a funnel-like receiving area 218 comprising a cut-away receiving portion 220, a guiding portion 222 and an abutment portion 224. Generally, the cut-away receiving portions 220 are positioned such that a top width of the divider wall 216 is less than the interface width 140 of the mating interface 138 so as to allow a medical professional to position the mating interface 138, and corresponding any tissue captured by the first tip 112, second tip 122 and dual tips 136a, 136b in the proper position and orientation with respect to the insertion head 208. The medical professional can then direct the mating interface 138 such that the interface wall 143 comes into abutting contact with divider wall 216 to position the tissue and first tip 112, second tip 122 and dual tips 136a, 136b at the proper fastening depth for skin stapler 202 along a Y plane defined through the midpoints of the positioning guides 214a, 214b as illustrated in FIG. 15. As the interface wall 143 approaches the divider wall 216, the dual tips 136a, 136b contact the guiding portion 222 and abutment portion 224 along the interface depth 142 wherein the guiding portion 222 and abutment portion 224 position the tissue captured by first tip 112, second tip 122 and dual tips 136a, 136b at a proper spaced apart distance along a Z plane wherein the Z plane is transversely oriented to an X plane defined through the center of divider wall 216. To further promote tissue positioning with respect to the insertion head 208, a pair of capture arms 226a, 226b can be attached to the skin stapler 202 for capturing, gripping and positioning tissue with respect to the insertion head 208. As illustrated in FIG. 17, each of the capture arms 226a, 226b can comprise an access region 228 and a gripping region 229 having a plurality of gripping member 230 shown in FIG. 17, or alternatively, ridges and other similar gripping arrangements to assist with maintaining tissue position relative to the positioning guides 214a, 214b. As illustrated in FIG. 18, another alternative embodiment of gripping head 208 can comprise an interface shelf 231 on divider wall 216 wherein the mating interface 138 is positionable over the interface shelf 231 for positioning tissue captured by first tip 112, second tip 122 and dual tips 136a, 136b in the proper position and orientation with respect to the insertion head 208.

Although the present invention has been described with respect to the various embodiments, it will be understood that numerous insubstantial changes in configuration, arrangement or appearance of the elements of the present invention can be made without departing from the intended scope of the present invention. Accordingly, it is intended that the scope of the present invention be determined by the claims as set forth.

What is claimed:

1. A wound closure system comprising:
    a sequential tissue forceps comprising a first arm, a second arm and a central arm, both the first arm and second arm having a tip end and an opposite end and the central arm having a tip portion and an opposite end, the tip portion defining dual tips separated by an interface width, the central arm operably positioned between the first arm and the second arm and operably joined to the first arm and the second arm proximate the opposite ends of the first arm, the second arm and the central arm with a first spring constant being defined relative between the first arm and the central arm and a second spring constant being defined relative between the second arm and the central arm, the second spring constant being greater than the first spring constant such that a manual force applied to squeeze the first arm and the second arm together initially causes approximation of the tip end of the first arm and one of the dual tips of the central arm to grasp a first side of a tissue wound therebetween and subsequently causes approximation of the tip end of the second arm and the other of the dual tips of the central arm to grasp a second side of the tissue wound therebetween residing substantially in the same plane; and
    a surgical fastening instrument comprising an insertion head and at least one tissue fastener wherein the insertion head interfaces with a mating interface defined between the dual tips of the central arm of the sequential tissue forceps such that the first and second sides of tissue are presented for deployment of the at least one tissue fastener into the first and second sides of tissue by the surgical fastening instrument.

2. The wound closure system of claim 1, wherein the insertion head comprises a plurality of staged receiving portions, each receiving portion being individually adapted to interface with the mating interface such that a plurality of interface positions are selectable for presentation of the first and second sides of tissue to the tissue fastener.

3. The wound closure system of claim 1, wherein the surgical fastening instrument comprises a subcuticular fastening instrument.

4. The wound closure system of claim 1, wherein the at least one tissue fastener comprises a bioabsorbable tissue fastener.

5. The wound closure system of claim 1, wherein the manual force applied to squeeze the first arm and the second arm so as to cause approximation of the tip end of the first arm and the corresponding dual tip of the central arm to grasp the first side of the tissue wound therebetween is between about 0.5 pounds to about 1.0 pounds.

6. The wound closure system of claim 5, wherein the manual force applied to squeeze the first arm and the second arm so as to cause approximation of the tip end of the second arm and the other of the dual tips of the central arm to grasp the second side of the tissue wound therebetween is between about 1.0 pounds to about 2.0 pounds.

7. A wound closure system comprising:
    a sequential tissue forceps comprising a first arm, a second arm and a central arm, both the first arm and second arm having a tip end and an opposite end and the central arm having a tip portion and an opposite end, the tip portion defining dual tips separated by an interface width, the central arm operably positioned between the first arm and the second arm and operably joined to the first arm and the second arm proximate the opposite ends of the first arm, the second arm and the central arm with a first spring constant being defined relative between the first arm and the central arm and a second spring constant being defined relative between the second arm and the central arm, the second spring constant being greater than the first spring constant such that a manual force applied to squeeze the first arm and the second arm together initially causes approximation of the tip end of the first arm and the corresponding dual tip of the central arm to grasp a first side of a tissue wound therebetween and subsequently causes approximation of the tip end of the second arm and the other dual tip of the central arm to grasp a second side of the tissue wound therebetween residing substantially in the same plane such that the first side and the second side are retained in a spaced apart relation having a pre-defined tissue separation distance; and
    a surgical fastening instrument comprising an insertion head and at least one tissue fastener wherein the insertion head interfaces with a mating interface defined between the dual tips of the central arm of the sequential tissue forceps wherein the fastener is deployed so as to capture the first side and the second side while retained at the pre-defined tissue separation distance.

* * * * *